United States Patent
Thomson et al.

(10) Patent No.: US 8,581,176 B2
(45) Date of Patent: Nov. 12, 2013

(54) METHOD FOR HIGH EFFICIENCY TANDEM MASS SPECTROMETRY

(75) Inventors: Bruce Thomson, Toronto (CA); Suzanne Ackloo, Whitby (CA)

(73) Assignee: DH Technologies Development Pte. Ltd., Singapore (SG)

( * ) Notice: Subject to any disclaimer, the term of this patent is extended or adjusted under 35 U.S.C. 154(b) by 251 days.

(21) Appl. No.: 12/788,403

(22) Filed: May 27, 2010

(65) Prior Publication Data

US 2011/0127419 A1 Jun. 2, 2011

Related U.S. Application Data

(60) Provisional application No. 61/181,409, filed on May 27, 2009.

(51) Int. Cl.
*H01J 49/00* (2006.01)

(52) U.S. Cl.
CPC .................................. *H01J 49/004* (2013.01)
USPC ......................................... 250/281; 250/282

(58) Field of Classification Search
USPC ................................................ 250/281–300
See application file for complete search history.

(56) References Cited

U.S. PATENT DOCUMENTS

| | | | |
|---|---|---|---|
| 4,629,478 A * | 12/1986 | Browner et al. | 250/288 |
| 5,877,495 A * | 3/1999 | Takada et al. | 250/288 |
| 6,107,623 A | 8/2000 | Bateman et al. | |
| 6,285,027 B1 | 9/2001 | Chernushevich et al. | |
| 6,586,727 B2 * | 7/2003 | Bateman et al. | 250/282 |
| 7,034,292 B1 | 4/2006 | Whitehouse et al. | |
| 7,049,584 B1 | 5/2006 | Whitehouse et al. | |
| 7,381,373 B2 | 6/2008 | Blake et al. | |
| 7,425,700 B2 * | 9/2008 | Stults et al. | 250/288 |
| 7,538,321 B2 * | 5/2009 | Ishimaru et al. | 250/288 |
| 2006/0138320 A1 * | 6/2006 | Bateman | 250/288 |
| 2010/0108878 A1 * | 5/2010 | Bateman et al. | 250/283 |

OTHER PUBLICATIONS

PCT Application No. PCT/CA2010/000797 Search Report dated Jul. 19, 2010.
PCT Application No. PCT/CA2010/000797 Written Opinion dated Jul. 19, 2010.

\* cited by examiner

*Primary Examiner* — Jack Berman

(57) ABSTRACT

A system and method for performing MS/MS of everything are provided. Ionisable materials separated in order of molecular weight in a plurality of mass ranges are received at a mass spectrometer system in a given order in time, each mass range comprising a respective center mass value and a respective width. The ionisable materials are ionised in the given order that each of the plurality of mass ranges are received, to form respective precursor ions in a respective given mass range. The respective precursor ions are filtered via a mass filter module, a mass scan range of the mass filter module synchronized with the given order in which each of the plurality of mass ranges are received. The respective precursor ions are fragmented, via a fragmentation module, to form respective product ions. The respective product ions are analyzed in a mass spectrometer module to produce product ion spectra.

18 Claims, 4 Drawing Sheets

METHOD FOR HIGH EFFICIENCY TANDEM MASS SPECTROMETRY

FIELD

The specification relates generally to mass spectrometry, and specifically to a method, system and apparatus for performing MS/MS of everything.

BACKGROUND

When performing tandem mass spectrometry, or MS/MS on a mixture of ions of unknown mass, there are a few approaches that have been attempted in the past. For example, a survey scan can be performed on precursor ions, and mass peaks of interest can first be identified, prior to selecting and fragmenting precursor ions. This can be characterized as an information dependent acquisition (IDA) method. However, this method can miss small peaks or components that are not identified as being of interest in the survey scan, and it can be inefficient if a large population of precursor ions is present, because it may be necessary to re-analyze the sample in order to identify all of the components. Alternatively, a mass filter can scan over a mass range of interest and acquire MS/MS on every precursor ion. This can be characterized as an MS/MS of everything method. While this avoids the need for survey scans and does not require any decisions about which precursor ions to select for MS/MS it is inefficient and slow, especially when the mass range of interest is large, as again significant amounts of sample are wasted. In a simple example, if the mass range of interest for a sample is 300 to 1000 amu, and the mass filter that selects the precursor ion has unit mass resolution (a peak width of approximately 1 amu), then MSMS spectra can be acquired in 1 amu steps from m/z 300 to 1000. Since most samples are analyzed by LC/MS, this requires acquiring 700 MS/MS spectra every few seconds, or even every second, sufficiently fast that at least one, and preferably more than one, complete MS/MS of everything acquisition is performed during each LC peak.

SUMMARY

A first aspect of the specification provides a method for performing MS/MS of everything in a mass spectrometer system. The method comprises receiving, at the mass spectrometer system, ionisable materials separated in order of molecular weight in a plurality of mass ranges, each mass range comprising a respective center mass value and a respective width, the plurality of mass ranges received in a given order in time. The method further comprises ionising the ionisable materials in the given order that each of the plurality of mass ranges are received, to form respective precursor ions in a respective given mass range. The method further comprises filtering the respective precursor ions via a mass filter module, a mass scan range of the mass filter module synchronized with the given order in which each of the plurality of mass ranges are received. The method further comprises fragmenting the respective precursor ions, via a fragmentation module, to form respective product ions. The method further comprises analyzing the respective product ions in a mass spectrometer module to produce product ion spectra.

The method can further comprise using a predictive model to establish a relationship between an average molecular weight of the respective ionisable materials and a time that the respective ionisable materials are received. The relationship can be established by a calibration curve. The relationship can be established via a look-up table.

The mass scan range of the mass filter module can comprise a center value that is synchronized in time with the center mass value of each of the plurality of mass ranges received in the given order.

A width of the mass scan range of the mass filter module can be one of substantially equal to the respective width of each of the plurality of mass ranges, and less than the respective width of each of the plurality of mass ranges. At least one of the width of the mass scan range and a width of the plurality of mass ranges can change as a function of time.

The product ion spectra can be acquired for each the respective precursor ion mass-to-charge (m/z) value within the mass scan range of the mass filter module.

Multiple reaction monitoring can be performed for at least a subset of pairs of respective precursor ions and product ions, each respective precursor ion falling within a respective mass scan range of the mass filter module.

A second aspect of the specification provides a system for performing MS/MS of everything. The system comprises an ionisation module enabled to: receive ionisable materials, from a mass separation system separated in order of molecular weight in a plurality of mass ranges, each of the mass ranges comprising a respective center mass value and a respective width, the plurality of mass ranges received in a given order in time; and ionise the ionisable materials in the given order that each of the plurality of mass ranges are received, to form respective precursor ions in a respective given mass range. The system further comprises a mass filter module enabled to filter the respective precursor ions, a mass scan range of the mass filter module synchronizable with the given order in which each of the plurality of mass ranges are received. The system further comprises a fragmentation module enabled to fragment the respective precursor ions to form respective product ions. The system further comprises a mass spectrometry module enabled to analyze the respective product ions to produce product ion spectra.

The system can further comprise the mass separation module.

The mass separation module can comprise at least one of a size exclusion liquid chromatograph system for eluting the ionisable materials in order of molecular weight, and a capillary electrophoresis system.

The ion source module can comprise one of an electrospray ionisation (ESI) source connected to the mass separation module, and a matrix-assisted laser desorption/ionisation (MALDI) source, the MALDI source enabled to receive ionisable materials separated in order of molecular weight via a MALDI plate.

The mass spectrometry module can comprise a time of flight (TOF) detector.

The mass spectrometry module can be enabled to perform multiple reaction monitoring for at least a subset of pairs of respective precursor ions and product ions, each respective precursor ion falling within the one mass scan range.

BRIEF DESCRIPTIONS OF THE DRAWINGS

Embodiments are described with reference to the following figures, in which.

DETAILED DESCRIPTION OF THE EMBODIMENTS

Figure 1:
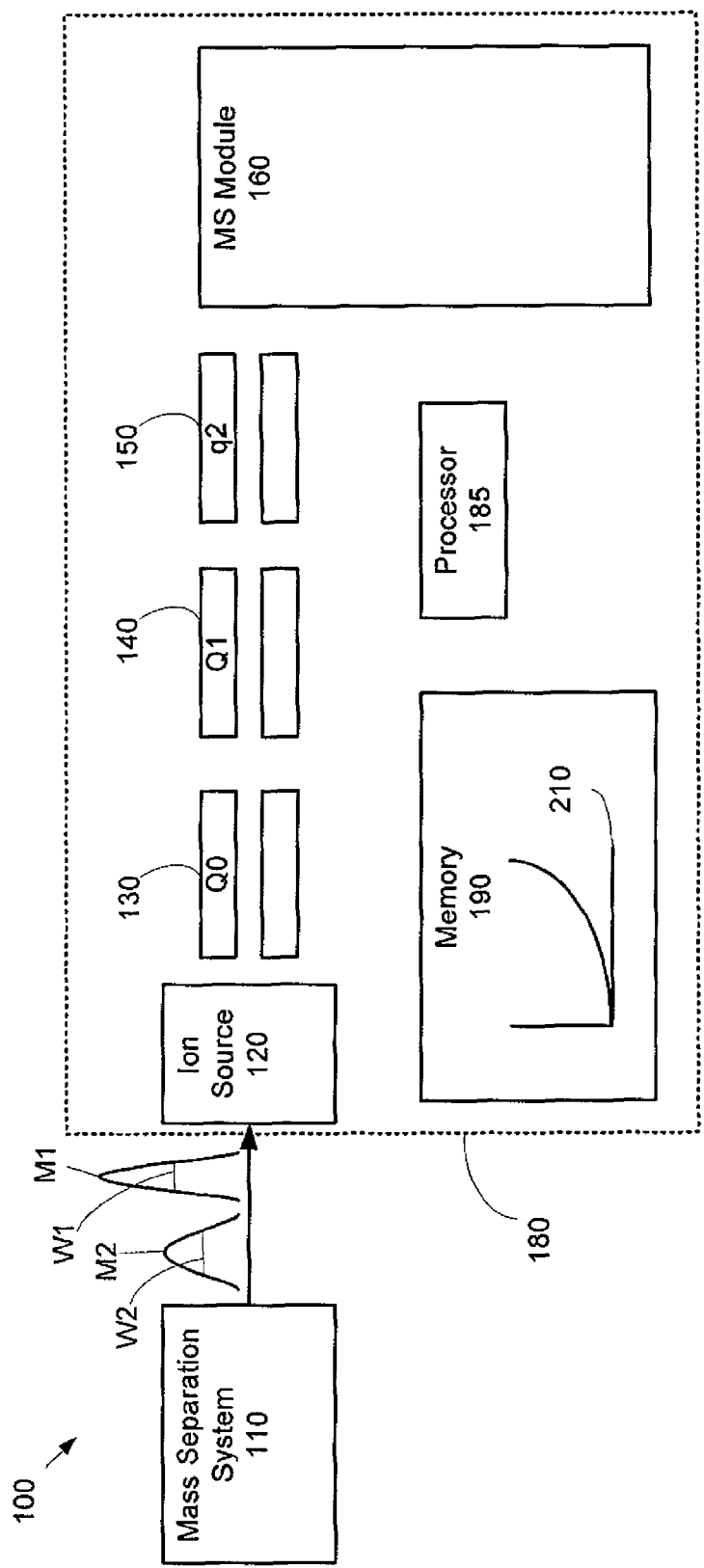
FIG. 1 depicts a system for performing mass spectrometry of everything, according to non-limiting embodiments.

FIG. 1 depicts a system 100 for performing MS/MS of everything, according to non-limiting embodiments. System 100 comprises a mass separation system 110, into which a sample of ionisable materials can be introduced, mass separation system 110 enabled to separate the ionisable materials into a plurality of mass ranges, such as mass range M1 and mass range M2, which are subsequently dispensed from mass separation system 110. In general, the ionisable materials separated into a plurality of mass ranges are dispensed from mass separation system 110 in an order of molecular weight and in a given order in time, as described below. In other words, mass separation system 110 has a time profile for dispensing ionisable materials in order of molecular weight, which can be established via a calibration process, for example, as described below.

Ionisable materials separated into the plurality of mass ranges are received at an ion source 120. Ion source 120 generally ionises the ionisable materials to produce precursor ions which are transferred to ion optics 130 (also identified as Q0 indicative that ion optics 130 take no part in the mass analysis). Precursor ions are transferred from ion optics 130 to a mass filter module 140 (also identified as Q1) which filters precursor ions, a mass scan range of mass filter module 140 synchronized with the given order in which each of the plurality of mass ranges are received, as described below. Precursor ions can then be transferred to a fragmentation module 150 (also identified as q2) for fragmentation, to form respective product ions, which are subsequently transferred to a mass spectrometer module 160 for mass analysis, resulting in production of product ion spectra.

Ion source 120, ion optics 130, mass filter module 140, fragmentation module 150 and mass spectrometer module 160 are generally interconnected in a mass spectrometer system 180 such that ions can be transported from ion source 120 to mass spectrometer module 160. In some embodiments, mass spectrometer system 180 can further comprise a processor 185, interconnected with a memory 190, processor 185 for controlling operation of mass spectrometer system 180 (and in some embodiments mass separation system 110), including but not limited to controlling ion source 120 to ionise the ionisable materials, and controlling transfer of ions between modules of mass spectrometer system. In particular, processor 185 controls mass filter module 140, as described below.

Furthermore, while not depicted, mass spectrometer system 180 can comprise any suitable number of vacuum pumps to provide a suitable vacuum in ion source 120, ion optics 130, mass filter module 140, fragmentation module 150 and/or mass spectrometer module 160. It is understood that in some embodiments a vacuum differential can be created between certain elements of mass spectrometer system 180: for example a vacuum differential is generally applied between ion source 120 and ion optics 130, such that ion source 120 is at atmospheric pressure and ion optics 130 are under vacuum. While also not depicted mass spectrometer system 180 can further comprise any suitable number of connectors, power sources, RF (radio-frequency) power sources, DC (direct current) power sources, gas sources (e.g. for ion source 120 and/or fragmentation module 150), and any other suitable components for enabling operation of mass spectrometer system 180.

In general, mass separation system 110 is enabled to separate ionisable materials in order of molecular weight, in a plurality of mass ranges. Furthermore, each mass range is characterized by a respective center mass value and a respective width. For example, in non limiting embodiments depicted in FIG. 1, two mass ranges, M1 and M2, of ionisable material are shown as dispensed from mass separation system 110, and received at ion source 120, in a given order in time, with the center mass value of mass range M1 less than the center mass value of mass range M2. In a particular non-limiting example described below with reference to FIG. 3, a center mass value of mass range M1 can be 200 amu, while a center mass value of mass range M2 can be 600 amu. However, it is understood that the center mass value of each mass range can be any suitable value, and is dependent on the mass separation system 110.

Mass range M1 comprises a respective width of W1 and mass range M2 comprises a respective width of W2. In some embodiments widths W1 and W2 can be substantially similar, while in other embodiments, widths W1 and W2 can be different (e.g. W1>W2 or W1<W2). In a particular non-limiting example described below with reference to FIG. 3, a width W1 of mass range M1 can be 60 amu, while a width W1 of mass range M1 can be 80 amu. However, it is understood that the width of each mass range can be any suitable value, and is dependent on the separation power of the mass separation system 110.

It is further understood that all ionisable materials of a sample introduced into mass separation system 110 within mass range M1 are substantially dispensed from mass separation system 110 at given time, and/or that substantially no ionisable materials within mass range M1 are left within the sample in mass separation system 110 once mass range M1 has been dispensed. Hence, ionisable materials from mass separation system 110 are received at ion source 120 in order of molecular weight, and that ionisable materials of a given molecular weight, once dispensed, will not appear in sample dispensed at a later time.

In a non-limiting example, mass separation system 110 can comprise a liquid chromatography system in which particles are separated based on their size and/or molecular weight; hence a sample of ionisable materials that is transported through a liquid chromatography system is eluted in order of molecular weight of the ionisable materials, from small to large or from large to small. Some conventional liquid chromatography systems separate compounds according to their polarity or chemical structure, but not necessarily in order of molecular weight. For example, at any point in time, there can be a range of masses being co-eluted, such as m/z 173, 381, 580, 942. Whatever the number of compounds, the sample being eluted can be characterized by a center value and a given width. However, in conventional liquid chromatography systems, not all sample of a given molecular weight inside the given width, is being eluted at a given time. In contrast, in a liquid chromatography system that separates materials according to molecular weight, or separates material in order of molecular weight, all ionisable materials within a given relatively narrow mass range (e.g. m/z between 100 and 200) are generally being eluted at a given time. One non-limiting example of a liquid chromatography system that separates material according to molecular weight is a size-exclusion liquid chromatography system, composed of a separation column and solvent delivery system that separates particles (molecules) according to their molecular weight, so that the particles are dispensed from the liquid chromatography system in order of molecular weight.

While mass separation system 100 will be describe with reference to a liquid chromatography system, it is understood that mass separation system 100 can comprise any suitable mass separation system in which ionisable materials are separated in order of molecular weight, in a plurality of mass ranges, characterized by a respective center mass value and a respective width. Another non-limiting example of a separation system is a capillary electrophoresis system.

In some embodiments, a predictive model can be used to establish a relationship between an average molecular weight (e.g. a centre mass value of a mass range) of respective ionisable materials and a time that respective ionisable materials are received at ion source 120 and/or dispensed (e.g. eluted) from mass separation system 110. For example, the average molecular weight of ionisable materials being dispensed from mass separation system 110 can be expressed as a function of time, $m=f(t)$, wherein m is mass, and $f(t)$ is a function of time. Such a function $f(t)$ can be established by performing a calibration of mass separation system 110, for example by introducing a sample of known ionisable materials in mass calibration system 110 and measuring the rate at which the ionisable materials are dispensed.

In other embodiments, the relationship between an average molecular weight (e.g. a centre mass value of a mass range) of respective ionisable materials and a time that respective ionisable materials are received at ion source 120 and/or dispensed (e.g. eluted) from mass separation system 110 can be established by a calibration curve (e.g. calibration curve 210), which can also be derived from a calibration. Similarly, the relationship can be established via a look-up table that can be derived from a calibration. A look-up table contains values of mass and corresponding times of elution.

In some embodiments, such a function $m=f(t)$, a calibration curve, a look-up table, and the like, can be supplied with mass separation system 110 (e.g. based on factory calibration), while in other embodiments, a function $m=f(t)$, a calibration curve, a look-up table, and the like can be obtained by performing a calibration with mass spectrometry system 180.

Figure 2:
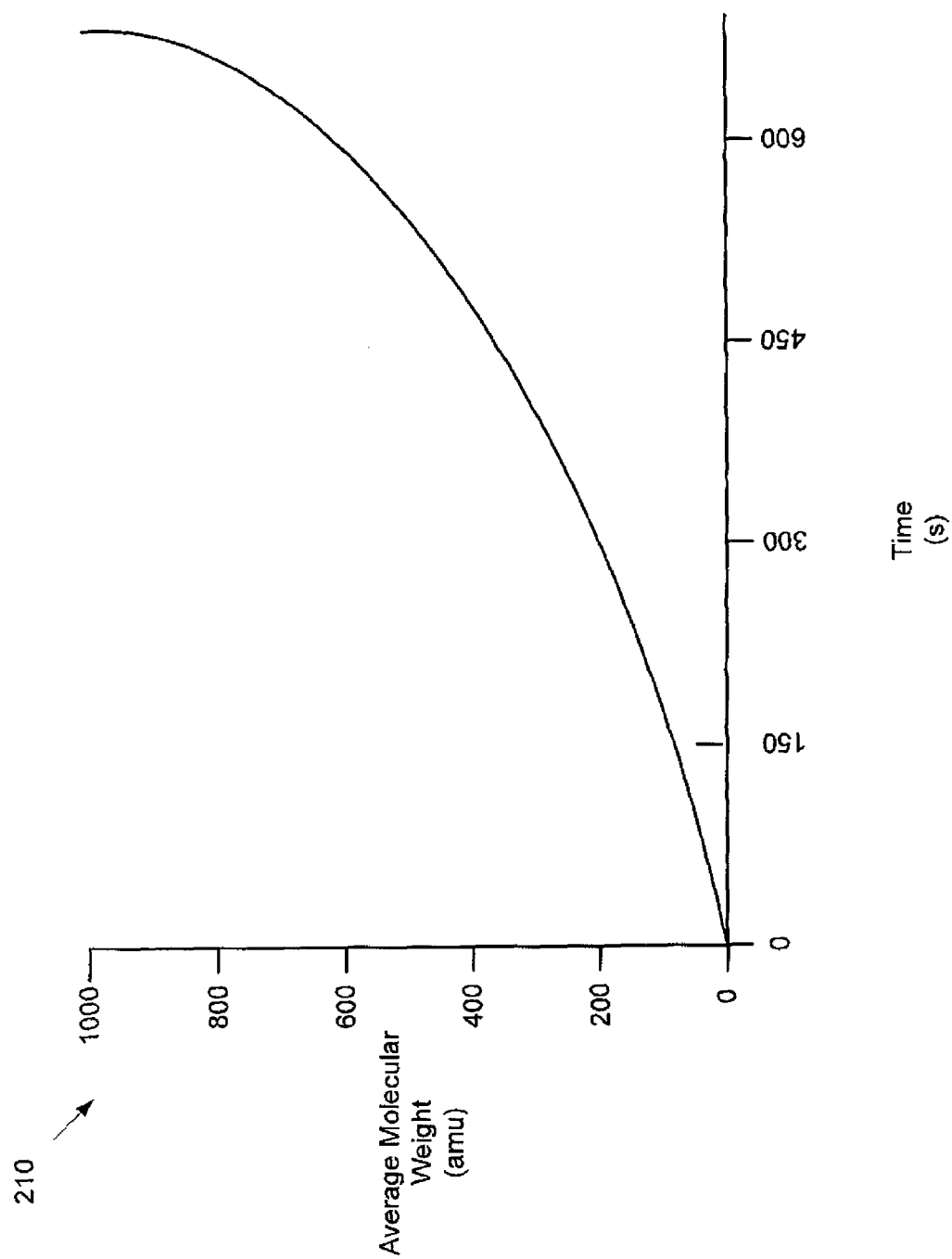
FIG. 2 depicts a calibration curve of a mass separation system, according to non-limiting embodiments.

For example, in some embodiments, a relationship between an average molecular weight of respective ionisable materials and a time that respective ionisable materials are received at ion source 120 and/or dispensed (e.g. eluted) from mass separation system 110 can be expressed as the calibration curve 210 of FIG. 2, in which can be stored in memory 190. In other embodiments, a look-up table and/or a function $m=f(t)$ can be stored in memory 190. In yet further embodiments, processor 185 can be pre-programmed with calibration curve 210, a look-up table and/or a function $m=f(t)$.

Ion source 120 comprises any suitable ion source for ionising ionisable materials received from mass separation system 110. Ion source 120 can include, but is not limited to, an electrospray ion source, an ion spray ion source, a corona discharge device, and the like. In these embodiments, mass separation system 100 is connected to ion source 120, such that ionisable materials are dispensed (e.g. eluted) from the mass separation system 100 to ion source 120 in any suitable manner.

In specific non-limiting embodiments, ion source 120 can comprise a matrix-assisted laser desorption/ionisation (MALDI) ion source. In these embodiments, mass separation system 110 can be enabled to dispense ionisable materials onto a MALDI plate in order of molecular weight of the ionisable materials, in a plurality of samples on the MALDI plate, which can generally comprise a translation stage. Correspondingly, ion source 120 is enabled to receive the ionisable materials via the MALDI plate, which can be inserted into the MALDI ion source, and ionise the samples of ionisable materials in any suitable order. In these embodiments, any suitable number of MALDI plates with any suitable number of samples dispensed there upon can be prepared prior to inserting them into the MALDI ion source; hence, the dispensing of a sample from mass separation system 110 is decoupled from ionisation of a sample.

In general, ion source 120 is enabled to receive the plurality of mass ranges of ionisable materials in a given order in time. In embodiments where mass separation system 110 is connected to ion source 120, the given order in time is dependent on the dispensing (e.g. elution) rate of ionisable materials from the mass separation system 110. In embodiments where mass separation system 110 dispenses materials onto a MALDI plate, the given order in time can be determined from the order in which sample is ionised from the MALDI plate (i.e. as a laser ionises sample from the MALDI plate).

In any event, ion source 120 is enabled to ionise ionisable materials in the given order that each of the plurality of mass ranges are received, to form respective precursor ions in a respective given mass range. For example, when mass range M1 is received at ion source 120, ionisable materials in mass range M1 are ionised to form precursor ions in mass range M1, and hence having substantially the same molecular weight as ionisable materials in mass range M1.

Precursor ions are then transferred to ion optics 130, for example via a vacuum differential and/or a suitable electric field(s). Ion optics 130 can generally comprise any suitable multipole, including but limited to a quadrupole rod set. Ion optics 130 are generally enabled to cool and focus precursor ions, and can further serve as an interface between ion source 120, at atmospheric pressure, and subsequent lower pressure vacuum modules of mass spectrometer system 180.

Precursor ions are then transferred to mass filter module 140, for example via any suitable vacuum differential and/or a suitable electric field(s), mass filter module 140 enabled to transmit ions to fragmentation module 150, within a specified mass to charge ratio (m/z) window, and to further scan through a range of masses such that the center m/z of the window changes with time, synchronized with the given order in which each of the plurality of mass ranges are received. Mass filter module 140 comprises any suitable apparatus enabled to filter ions within a specified mass-to-charge ratio (m/z) window, however in particular non-limiting embodiments, mass filter module 140 comprises a quadrupole rod set with suitable applied RF and DC fields applied thereto.

In particular, mass filter module 140 is enabled to filter precursor ions, a mass scan range of mass filter module 140 synchronized with the given order in which each of the plurality of mass ranges are received from mass separation system 110. For example, the mass scan range of mass filter module 140 can be controlled by processor 185 based on calibration curve 210, a look-up table and/or a function $m=f(t)$, as described above, for example as stored in memory 190. For example, in embodiments where mass separation system 110 is connected to ion source 120, the mass scan range of mass filter module 140 is synchronized with the dispensing/elution of ionisable materials from mass separation system 110, such that mass filter module 140 is scanning through each mass range as it is received from mass separation system 110 (allowing for additional time to ionise ionisable materials at ion source 120 and to transfer ions from ion source 120 through ion optics 130 to mass filter module 140, a time that is generally on the order of microseconds to a few milliseconds).

Figure 3:
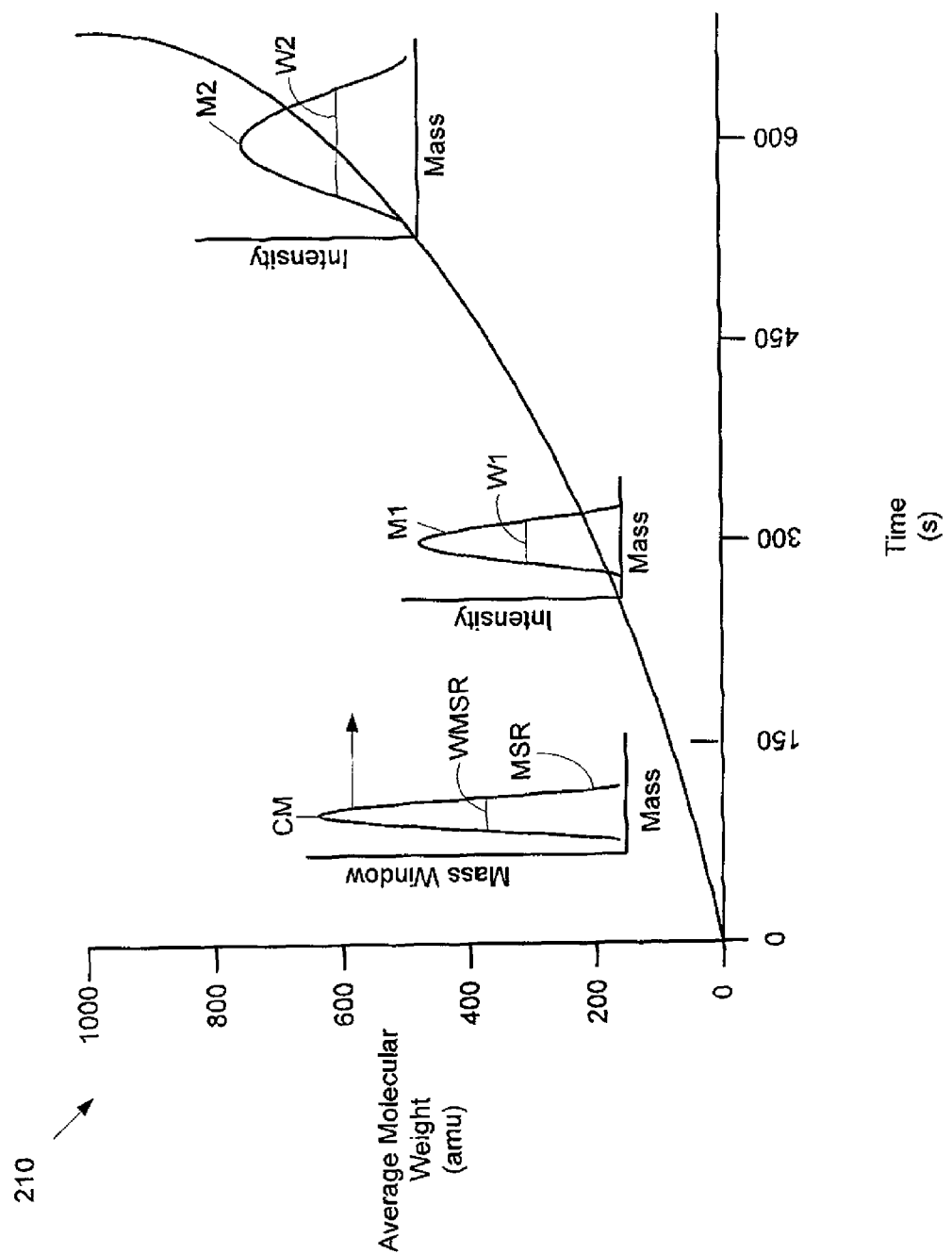
FIG. 3 depicts the calibration curve of FIG. 2 with a mass scan range of a mass filter module, and mass ranges of ionisable materials dispensed from a mass separation system depicted thereupon, according to non-limiting embodiments.

In a particular non-limiting example, the mass scan range of mass filter module 140 is depicted as a mass scan range MSR in FIG. 3, which is similar to FIG. 2, however with mass scan range MSR and mass ranges M1 and M2 depicted thereupon. It is understood that each of mass ranges M1 and M2 as depicted in FIG. 3 comprise a distribution of molecular weights of the ionisable materials being emitted at one time, the distribution having respective widths W1 and W2. The distributions as depicted in FIG. 3 are shown as a Gaussian shape, but other distribution shapes are possible, depending on the characteristics of the separation system 110. For example, the distribution shape may comprise a Lorentzian shape or a triangular shape. It is further understood that mass scan range MSR as depicted in FIG. 3 comprises a mass range centred on a given center mass value CM at any given time, with a width WMSR. In the non-limiting example, mass range M1 comprises a center mass value of 200 amu and a width W1 of 60 amu; furthermore, as depicted, mass range M1 is received at approximately t=5 minutes (300 seconds). The CM can then be 200 amu and the WMSR can be 60 amu. In some cases the WMSR can be set to be larger than 60 amu in order to ensure that all ions within the M1 distribution are analyzed. In other cases the WMSR can be set to less that 60 amu to analyze a narrower mass range. Similarly, in the non-limiting example, mass range M2 comprises a center mass value of 600 amu and a width W2 of 80 amu; furthermore, as depicted, mass range M2 is received at approximately t=10 minutes (600 seconds). In one mode of operation, the value of CM can be smoothly and continuously changed from 200 amu at 5 minutes up to 600 amu at 10 minutes, while mass filter module 140 is scanned. The scan range will be 60 amu in width (i.e. from m/z 170 to m/z 230) at 5 minutes time, and will increase smoothly and continuously to a range of 80 amu (i.e. from m/z 560 to m/z 640) at 10 minutes time. In some modes of operation the CM and/or the WMSR can change in steps or increments rather than in a continuous manner.

In any event, mass scan range MSR is synchronized with the given order in which each of the plurality of mass ranges are received, for example mass ranges M1 and M2. Furthermore, as the mass ranges that will be received from mass separation system 110 is generally unknown, mass filter module 140 will scan through all suitable mass ranges, for example from highest to lowest, such that no mass range from mass separation module 110 is unanalyzed. For example, centre mass (CM) value can start at a low value such as 100 amu and scan through to 1000 amu with a width WMSR of 50 amu; furthermore, the CM scan rate can comprise a suitable scan rate that maintains synchronization with the mass value that is dispensed or eluted from mass separation system 110. In a non-limiting example, if the CM value is scanned from 200 amu at 5 minutes up to 600 amu at 10 minutes, that corresponds to a scan rate of 80 amu per minute for the CM value of mass filter module 140., a rate selected to be synchronized with the rate at which the plurality of mass ranges are received. As the CM value is being scanned at 80 amu per minute, or 1.333 amu per second, mass filter module 140 can be scanned through 50 amu at a faster rate, for example 100 amu per second. The scan through 50 amu will then take 500 milliseconds. The CM value can be moved quasi-continuously at the rate of 80 amu per minute in the example above, adjusting the CM value by an amount of 0.666 amu after each 500 ms, i.e. after each scan through the WMSR scan range. This comprises a quasi-continuous scan of the CM value because the value is adjusted in small steps at each 0.5 second in time. In another non-limiting example, the CM value can be adjusted after every 10 second interval by an amount of 13.333 amu, so that the scan of the CM value is less continuous and more step-wise.

However, in general the CM scan rate of mass filter module 140 is determined from calibration curve 210 (or the equivalent).

In any event, center mass value CM is synchronized in time with the center mass value of each of the plurality of mass ranges received.

Width WMSR can be any suitable width, for example at least one of substantially equal to a respective width of each of the plurality of mass ranges, and less than a respective width of each of the plurality of mass ranges.

The mass range of the ionisable material that is dispensed can be expressed in units of molecular weight of the neutral molecule, units that may be expressed as atomic mass units (amu) or Daltons (Da). The mass of ions formed in the ion source is approximately the same as the mass of the neutral molecule, being different by usually only the mass of an electron or the mass of a proton (or more than one proton if the ion is multiply protonated). For the purposes of this description, the mass of the neutral and the mass of the ion can be considered to be substantially the same. Mass spectrometers separate ions according to their mass-to-charge ratio (m/z). The unit of m/z is sometimes called a Thomson (Th), but is also commonly also expressed in units of amu or Da.

In many examples, it is known that the ionisable materials that are dispensed or eluted from mass separation system 110 can form substantially singly charged ions. For example, pharmaceutical compound and metabolites, environmental contaminants such as pesticides and the like, industrial chemicals such as plasticizers and the like, are known to be ionized as singly charged ions in an ESI or APCI (atmospheric pressure chemical ionization) ion source. In some examples it is known that the ionisable materials will form multiply-charged ions. For example, peptides that are formed by a tryptic digest of a mixture of proteins are known to form mostly doubly-charged ions with lower amounts of triply-charged ions and quadruply charged ions.

In embodiments where the ions are known to be mostly singly charged, the mass range scanned by mass filter module 140 and the mass range dispensed from mass separation system 110 can be substantially the same. This is because mass spectrometer module 160 analyzes ions according to mass-to-charge ratio m/z, which is the same as the mass if the charge state (z) is 1. In embodiments where the ions are known to be mostly doubly-charged ions (peptides for example), the mass range that is scanned by mass filter module 140, and the CM value, can be adjusted according to the known charge state. For example, if the mass range M1 is 200 amu, and the width of the mass range is 50 amu, then the CM value can be adjusted to 100 amu and the WMSR to 25 amu. In the above non-limiting example, the scan rate of CM can then be set to 40 amu per minute and the width WMSR can be set to 25 amu. In embodiments where the materials can form a wide range of charge states, CM value and WMSR can be selected according to the charge state. In some embodiments, it is known that the materials can form both singly, doubly and triply charged ions (some of each). In some other embodiments, it is known that some materials can from only singly-charged ions, and other materials can form doubly-charged ions, and other materials can form triply-charged ions. In this case, the CM values can be selected according to the known charge states of the ions formed in the ion source, and the CM value can be programmed to step from that appropriate for 1+ ions to that appropriate for 2+ ions to that appropriate for 3+ ions, scanning through the appropriate WMSR for each range. For example, if mass separation system 110 is dispensing material of center mass value 600 at 5 minutes, and it is known that some materials can be of 1+ charge state, some of 2+ charge state and some of 3+ charge state, then the CM value can be set to 600 and the WMSR set to 50 for one scan of the mass filter module 140 (requiring 500 ms in the example scan rate above). Then CM can be set to 300 and the WMSR set to 25 for a second scan of mass filter module 140. Then the CM value can be set to 200 and the WMSR set to 17 for a third scan of mass filter module 140. Then the cycle of the three values of CM can be repeated, each cycle comprising approximately 1.5 seconds in total. As the dispensed mass range changes, the CM values can be increased in synchronization with the mass range, cycling between the three charge states. In some embodiments, system 100 can further comprise an ion mobility module, which separates ions according to the charge state (the ion mobility module must follow after ion source 120). In these embodiments, the separation is already in m/z units, and the CM of mass filter module 140 and the mass range dispensed by ion mobility module will be substantially the same.

In embodiments where ion source 120 comprises a MALDI ion source, the given order in which ionisable materials are received and ionised is dependent on the order in which a laser in the MALDI source ionises each of the plurality of samples on the MALDI plate, as well as the mass range of each sample on the MALDI plate. For example, calibration curve 210 can be utilized to control and determine the mass range of each of the plurality of samples on the MALDI plate as each sample is dispensed. Furthermore, once the MALDI plate is received at ion source 120, the laser ionisation of each of the plurality of samples can be performed in any suitable order, the mass scan range of mass filter module 140 synchronized with the ionisation of each of the plurality of samples. In these embodiments, mass filter module 140 will scan through all suitable mass ranges, as synchronized with an order in which samples on the MALDI plate are ionized, the mass range of each sample on the MALDI plate known from calibration curve 210 (or the equivalent).

In any event, as mass filter module 140 scans through each mass range, filtered pre-cursor ions are transmitted to fragmentation module 150 for fragmentation such that fragmented respective product ions are produced for each mass range.

In some embodiments, multiple reaction monitoring can be performed for at least a subset of pairs of respective precursor ions and product ions, each respective precursor ion falling within a respective mass scan range of mass filter module 140.

Once fragmented, product ions are transferred to mass spectrometer module 160 for analysis and production of product ion spectra. Mass spectrometer module 160 can comprise any suitable mass spectrometer module including, but not limited to, a time of flight (TOF) mass spectrometry module, a quadrupole mass spectrometry module, a linear ion trap (LIT) module and the like. In any event, product ion spectra are acquired for each respective precursor ion mass-to-charge (m/z) value that is selected by mass filter module 140.

Figure 4:
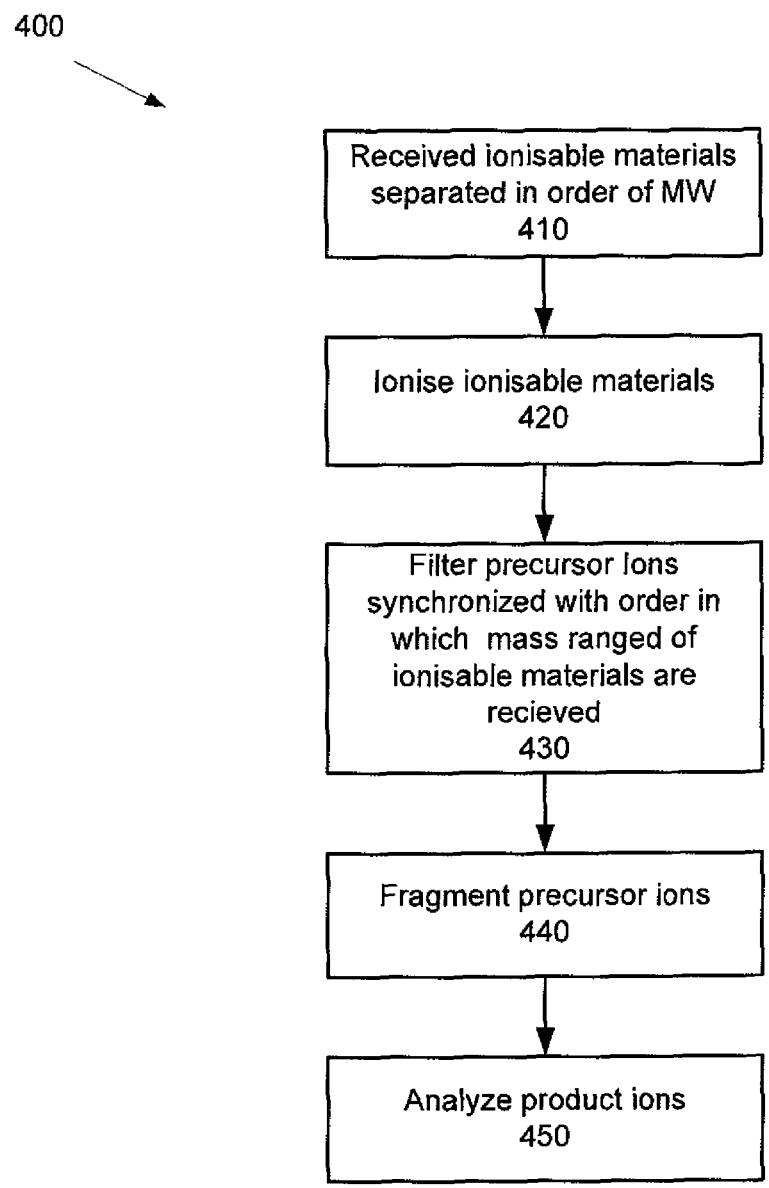
FIG. 4 depicts a method for performing mass spectrometry of everything, according to non-limiting embodiments.

Attention is now directed to FIG. 4 which depicts a method 400 for performing MS/MS of everything. In order to assist in the explanation of the method 400, it will be assumed that the method 400 is performed using the system 100. Furthermore, the following discussion of the method 400 will lead to a further understanding of the system 100 and its various components. However, it is to be understood that the system 100 and/or the method 400 can be varied, and need not work exactly as discussed herein in conjunction with each other, and that such variations are within the scope of present embodiments.

At step 410 ionisable materials are received, separated in order of molecular weight in a plurality of mass ranges, each mass range characterized by a respective center mass value and a respective width, the plurality of mass ranges received in a given order in time. For example, mass ranges M1 and M2 can respectively comprise a center mass value of 200 amu and 600 amu, respectively and a width 60 amu and 80 amu respectively, as described above with respect to FIG. 3. Furthermore, the ionisable materials can be received at ion source 120, from mass separation system 110 via elution from a size exclusion liquid chromatography system and/or via a MALDI plate, as described above.

At step 420, the ionisable materials are ionised in the given order that each the plurality of mass ranges are received, to form respective precursor ions in a respective given mass range, for example via ion source 120.

At step 430, the respective precursor ions are filtered, e.g. via mass filter module 140, a mass scan range of mass filter module 140 synchronized with the given order in which each of the plurality of mass ranges are received. Such a synchronization can be performed based a calibration curve (e.g. calibration curve 210) or the equivalent (e.g. function, m=f(t), and a look-up table, as described above). Hence, as respective precursor ions arrive at mass filter module 140, the scan range of mass filter module 140 is synchronized to transmit ions in the range of the respective precursor ions. Such a synchronization is generally enabled by mass separation module 110 having a known time profile for dispensing a plurality of given mass ranges of ionisable material, as described above.

At step 440, the respective precursor ions are fragmented, e.g. via fragmentation module 150, to form respective product ions. At step 450, product ions are analyzed, for example via mass spectrometer module 160, to produce product ion spectra.

Hence, efficient performance of MS/MS of everything can be provided by combining a mass separation system (e.g. mass separation system 110) having a known time profile for dispensing a plurality of given mass ranges of ionisable material with a mass spectrometry system (e.g. mass spectrometer system 180) in which the filtering of ions prior to fragmentation is synchronized with the known time profile by synchronizing the mass scan range of a mass filter module (e.g. mass filter module 140) with a given order in which each of the plurality of mass ranges are received. The mass range of precursor ions at any given time is thus narrow and predictable and mass filter module 140 can be scanned over a narrow mass range, with the actual range dependent on the length of time the mass separation system has been operating. Sample is not wasted, and there is no need to perform a survey scan and/or collect information about a sample (i.e. perform IDA) prior to performing mass spectrometry analysis. Such a method can also be used with iTRAQ-derivatized samples to improve efficiency in a precursor scan mode. In this method, peptide ions that are labeled with a signature ion of a known mass value can be analyzed. The presence of a specific signature ion indicates the presence of a peptide, and the relative amounts of the signature ions can indicate the relative amounts of the peptides. In some embodiments the intensities of the known signature ions can be monitored with mass spectrometer module 160, while scanning mass filter module 140 through the known mass range to determine the precursor ion mass values. In this case method 400 can be used to provide a narrow mass range for the scan of mass filter module 140, synchronized with the mass range of the material dispensed from mass separation module 110. Hence, the efficiency of sample utilization can be improved when compared to the conventional method where the entire mass range must be continuously scanned by the mass filter module 140.

Those skilled in the art will appreciate that in some embodiments, the functionality of system 100 can be implemented using pre-programmed hardware or firmware elements (e.g., application specific integrated circuits (ASICs), electrically erasable programmable read-only memories (EEPROMs), etc.), or other related components. In other embodiments, the functionality of system 100 can be achieved using a computing apparatus that has access to a code memory (not shown) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Alternatively, the computer-readable program code could be stored remotely but transmittable to these components via a modem or other interface device connected to a network (including, without limitation, the Internet) over a transmission medium. The transmission medium can be either a non-wireless medium (e.g., optical and/or digital and/or analog communications lines) or a wireless medium (e.g., microwave, infrared, free-space optical or other transmission schemes) or a combination thereof.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

What is claimed is:

1. A method for performing MS/MS of everything in a mass spectrometer system, the method comprising:
   receiving from a mass separation system, ionisable materials separated in order of molecular weight in a plurality of mass ranges, each said mass range comprising a respective center mass value and a respective width, said plurality of mass ranges received in a given order in time;
   ionising said ionisable materials in said given order that each of said plurality of mass ranges are received, to form respective precursor ions in a respective given mass range;
   filtering said respective precursor ions via a mass filter module, to repetitively scan a selected mass range from the plurality of mass ranges, said mass scan range of said mass filter module comprises a center value that is synchronized in time with said center mass value of each of said plurality of mass ranges received in said given order;
   fragmenting said respective precursor ions, via a fragmentation module, to form respective product ions; and
   analyzing said respective product ions in a mass spectrometer module to produce product ion spectra.

2. The method of claim 1, further comprising using a predictive model to establish a relationship between an average molecular weight of said respective ionisable materials and a time that said respective ionisable materials are received.

3. The method of claim 2, wherein said relationship is established by a calibration curve.

4. The method of claim 2, wherein said relationship is established via a look-up table.

5. The method of claim 1, wherein a width of said mass scan range of said mass filter module is one of substantially equal to said respective width of each of said plurality of mass ranges, and less than said respective width of each of said plurality of mass ranges.

6. The method of claim 5, wherein at least one of said width of said mass scan range and a width of said plurality of mass ranges changes as a function of time.

7. The method of claim 1, wherein said product ion spectra are acquired for each said respective precursor ion mass-to-charge (m/z) value within said mass scan range of said mass filter module.

8. The method of claim 1, wherein multiple reaction monitoring is performed for at least a subset of pairs of respective precursor ions and product ions, each respective precursor ion falling within a respective mass scan range of said mass filter module.

9. A system for performing MS/MS of everything, the system comprising:
   an ionisation module enabled to:
      receive ionisable materials, from a mass separation system separated in order of molecular weight in a plurality of mass ranges, each said mass range comprising a respective center mass value and a respective width, said plurality of mass ranges received in a given order in time; and
      ionise said ionisable materials in said given order that each of said plurality of mass ranges are received, to form respective precursor ions in a respective given mass range;
   a mass filter module enabled to filter said respective precursor ions, to repetitively scan a selected mass range from the plurality of mass ranges, said mass scan range of said mass filter module comprises a center value that is synchronizable in time with said center mass value of each of said plurality of mass ranges received in said given order;
   a fragmentation module enabled to fragment said respective precursor ions to form respective product ions; and
   a mass spectrometry module enabled to analyze said respective product ions to produce product ion spectra.

10. The system of claim 9, further comprising said mass separation system.

11. The system of claim 10, wherein said mass separation system comprises at least one of a size exclusion liquid chromatograph system for eluting said ionisable materials in order of molecular weight and a capillary electrophoresis system.

12. The system of claim 9, wherein said ion source module comprises one of an electrospray ionisation (ESI) source connected to said mass separation module, and a matrix-assisted laser desorption/ionisation (MALDI) source, said MALDI source enabled to receive ionisable materials separated in order of molecular weight via a MALDI plate.

13. The system of claim 9, wherein said mass spectrometry module comprises a time of flight (TOF) detector.

14. The system of claim 9, wherein said mass spectrometry module is enabled to perform multiple reaction monitoring for at least a subset of pairs of respective precursor ions and product ions, each respective precursor ion falling within said one mass scan range.

15. The system of claim 9, further comprising a memory storing a predictive model of a relationship between an average molecular weight of said respective ionisable materials and a time that said respective ionisable materials are received, and wherein said relationship comprises at least one of a calibration curve and a look-up table.

16. The system of claim 9, wherein a width of said mass scan range of said mass filter module is at least one of substantially equal to said respective width of each of said plurality of mass ranges, and less than said respective width of each of said plurality of mass ranges.

17. The system of claim 16, wherein at least one of said width of said mass scan range and a width of said plurality of mass ranges changes as a function of time.

18. The system of claim 9, wherein said mass spectrometry module is enabled to acquire product ion spectra for each said respective precursor ion mass-to-charge (m/z) value within said mass scan range of said mass filter module.

* * * * *